United States Patent
Hsieh et al.

(10) Patent No.: US 8,501,286 B2
(45) Date of Patent: Aug. 6, 2013

(54) REACTIVE MONOMER OF LIQUID CRYSTAL AND LIQUID CRYSTAL PANEL

(75) Inventors: Chung-Ching Hsieh, Guangdong (CN); Chengming He, Shenzhen (CN)

(73) Assignee: Shenzhen China Star Optoelectronics Technology Co., Ltd., Guangdong (CN)

(*) Notice: Subject to any disclaimer, the term of this patent is extended or adjusted under 35 U.S.C. 154(b) by 0 days.

(21) Appl. No.: 13/259,269

(22) PCT Filed: Aug. 11, 2011

(86) PCT No.: PCT/CN2011/078311
§ 371 (c)(1),
(2), (4) Date: Sep. 23, 2011

(87) PCT Pub. No.: WO2013/013427
PCT Pub. Date: Jan. 31, 2013

(65) Prior Publication Data
US 2013/0021568 A1    Jan. 24, 2013

(30) Foreign Application Priority Data

Jul. 22, 2011    (CN) .......................... 2011 1 0206568

(51) Int. Cl.
*C09K 19/38*    (2006.01)
*C09K 19/20*    (2006.01)
*C09K 19/12*    (2006.01)
*G02F 1/1337*   (2006.01)

(52) U.S. Cl.
USPC .. 428/1.2; 428/1.25; 252/299.66; 252/299.67

(58) Field of Classification Search
USPC .................... 428/1.1, 1.2, 1.25; 252/299.66, 252/299.67
See application file for complete search history.

(56) References Cited

U.S. PATENT DOCUMENTS
2011/0272631 A1    11/2011    Saito

FOREIGN PATENT DOCUMENTS
WO    WO 2010/084823 A1    7/2010

*Primary Examiner* — Shean C Wu
(74) *Attorney, Agent, or Firm* — Ditthavong Mori & Steiner, P.C.

(57) ABSTRACT

The present invention discloses a reactive monomer of liquid crystal. The reactive monomer of liquid crystal is added with at least one fluoro group. Because hydrocarbon bonds of a side chain of polyimide surface of an alignment film has a fluorophobic effect, the fluoro group of the reactive monomer of liquid crystal can lower the interaction between the polyimide surface of the alignment film and the reactive monomer of liquid crystal to thus evenly deposit the liquid crystal composition containing the reactive monomers of liquid crystal onto the polyimide surface of the alignment film. Thus, it can avoid from occurring the phenomenon of drop Mura defect occurred during implementing the ODF technology.

4 Claims, 2 Drawing Sheets

REACTIVE MONOMER OF LIQUID CRYSTAL AND LIQUID CRYSTAL PANEL

FIELD OF THE INVENTION

The present invention relates to a reactive monomer of liquid crystal and a liquid crystal panel, and more particularly to a reactive monomer of liquid crystal added with a fluoro group (F—) and a liquid crystal panel having the reactive monomer of liquid crystal.

BACKGROUND OF THE INVENTION

Traditionally, the injection method of liquid crystal during manufacturing a liquid crystal panel is to slowly inject liquid crystal into a space between two combined glass substrates according to the capillarity principle, but the disadvantage is that the method consumes much time and waste material of liquid crystal The foregoing injection method of liquid crystal is gradually replaced by a one-drop filling (ODF) technology. In the one-drop filling technology, liquid crystal is firstly and directly dropped onto a glass substrate through a liquid crystal dropping device, and then the glass substrate is aligned and combined with the other glass substrate. This new technology can substantially save filling time of liquid crystal and material of liquid crystal.

However, when manufacturing some liquid crystal panel having liquid crystal alignment capable of improving visual angles, the liquid crystal is dropped onto an alignment film of a substrate by the one-drop filling technology, wherein the alignment film is impacted by the drops of liquid crystal to thus cause the phenomenon of drop Mura defect occurred on a finished product.

For more details, referring now to FIG. 1A, a schematic view of a traditional one-drop filling (ODF) technology dropping a liquid crystal composition onto an alignment film of a transparent substrate is illustrated. Referring to FIGS. 1B and 1C, schematic views of reactive monomers 1' of liquid crystal in the liquid crystal composition deposited on a polyimide surface 2' of the alignment film are illustrated, wherein the phenomenon of drop Mura defect is caused because different amounts of the reactive monomers 1' of liquid crystal are unevenly deposited on the polyimide surface 2' of the alignment film on the transparent substrate.

The reactive monomers 1' of liquid crystal used by the traditional ODF technology have the following molecular formula (I):

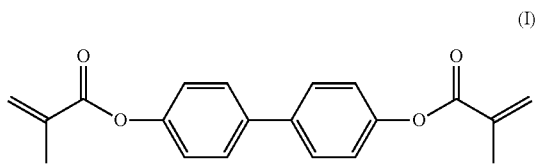 [SMILES: C=C(C)C(=O)Oc1ccc(-c2ccc(OC(=O)C(=C)C)cc2)cc1]

(I)

When changing the cell gap of the liquid crystal to be smaller than 3.8 μm, it causes that the traditional reactive monomers of liquid crystal can not be widely dispersed on a large area of the polyimide surface of the alignment film, and thus different amounts of the reactive monomers of liquid crystal are unevenly deposited on the polyimide (PI) surface of the alignment film, as shown in FIG. 1. Thus, when the cell gap of the liquid crystal is smaller than 3.8 μm, there will be the phenomenon of drop Mura defect on the liquid crystal panel.

Referring now to Tab. 1, observed results of the phenomenon of drop Mura defect for of the traditional reactive monomer of liquid crystal under conditions of various cell gaps of liquid crystal are shown in Tab. 1. Apparently, as shown in Tab. 1, when the cell gap of the liquid crystal is smaller than 3.8 μm, there will be the phenomenon of drop Mura defect.

TABLE 1

| Cell gap | reactive monomer | phenomenon of drop Mura defect |
| --- | --- | --- |
| 3.8 μm | molecular formula (I) | Few |
| 3.5 μm | molecular formula (I) | Many |
| 3.3 μm | molecular formula (I) | Many |
| 3.0 μm | molecular formula (I) | More |

For more details, the reason causing the phenomenon of drop Mura defect is that the interaction between the reactive monomers of liquid crystal and the PI surface of the alignment film is excess, and thus it is disadvantageous to evenly deposit the liquid crystal composition containing the reactive monomers of liquid crystal onto the polyimide surface of the alignment film.

As a result, it is necessary to provide a reactive monomer (RM) of liquid crystal having a modified group to solve the problems existing in the conventional technologies, as described above.

SUMMARY OF THE INVENTION

A primary object of the present invention is to provide a reactive monomer (RM) of liquid crystal, which contains fluoro group (F—), so that a fluorophobic effect will be generated between the reactive monomer of liquid crystal and hydrocarbon bonds of a side chain of a polyimide surface of an alignment film, so as to lower the interaction between the reactive monomer (RM) of liquid crystal and the polyimide surface of the alignment film and to thus avoid from occurring the phenomenon of drop Mura defect.

To achieve the above object, the present invention provides a reactive monomer of liquid crystal, wherein the reactive monomer of liquid crystal is contained in a liquid crystal composition to disperse the liquid crystal composition onto a polyimide surface of an alignment film, the reactive monomer of liquid crystal contains a fluoro group (F—) and has a molecular formula, as follows:

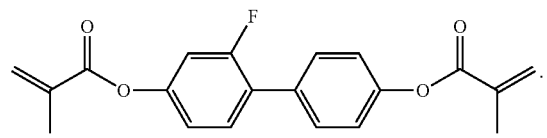 [SMILES: C=C(C)C(=O)Oc1ccc(-c2ccc(OC(=O)C(=C)C)cc2F)cc1]

The liquid crystal composition is a liquid crystal composition of a one-drop filling (ODF) technology.

To achieve the above object, the present invention further provides a reactive monomer of liquid crystal, wherein the reactive monomer of liquid crystal is contained in a liquid crystal composition to disperse the liquid crystal composition onto a polyimide surface of an alignment film, characterized in that: the reactive monomer of liquid crystal contains at least one fluoro group (F—) and has a molecular formula, as follows:

(II)

wherein n is greater than or equal to 1.

In one embodiment of the present invention, the reactive monomer of liquid crystal has a molecular formula, as follows:

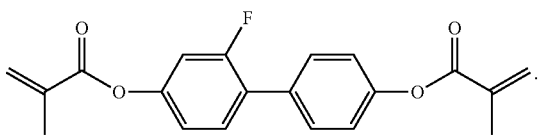 [SMILES: C=C(C)C(=O)Oc1ccc(-c2ccc(OC(=O)C(=C)C)cc2F)cc1]

In one embodiment of the present invention, the liquid crystal composition is a liquid crystal composition of a one-drop filling (ODF) technology.

A secondary object of the present invention is to provide a liquid crystal panel, having a transparent substrate and an alignment film, wherein a polyimide surface of the alignment film is dispersed with at least one type of reactive monomer of liquid crystal, the reactive monomer of liquid crystal causes the liquid crystal composition to be dispersed onto the polyimide surface of the alignment film, the reactive monomer of liquid crystal contains at least one fluoro group (F—) and has the molecular formula (II), as described above.

In one embodiment of the present invention, the reactive monomer of liquid crystal has a molecular formula, as follows:

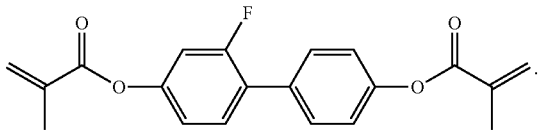 [SMILES: C=C(C)C(=O)Oc1ccc(-c2ccc(OC(=O)C(=C)C)cc2F)cc1]

In one embodiment of the present invention, the liquid crystal composition is a liquid crystal composition of a one-drop filling (ODF) technology.

In one embodiment of the present invention, the transparent substrate is a glass substrate.

In one embodiment of the present invention, the transparent substrate is a flexible polymer substrate or an inflexible polymer substrate.

The positive effect of the present invention is that: the reactive monomer of liquid crystal is added with the fluoro group (F—), wherein hydrocarbon bonds of a side chain of polyimide (PI) surface of an alignment film has a fluorophobic effect, so that the fluoro group of the reactive monomer of liquid crystal can lower the interaction between the polyimide (PI) surface of the alignment film and the reactive monomer (RM) of liquid crystal to thus evenly deposit the liquid crystal composition containing the reactive monomers of liquid crystal onto the polyimide (PI) surface of the alignment film, so as to avoid from occurring the phenomenon of drop Mura defect occurred during implementing the ODF technology.

Wherein

The numeral 1 and 1' represents reactive monomers of liquid crystal; and The numeral 2 and 2' represents polyimide (PI) surface.

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings.

According to a preferred embodiment of the present invention, the present invention provides a reactive monomer of liquid crystal, wherein the reactive monomer of liquid crystal is contained in a liquid crystal composition to disperse the liquid crystal composition onto a polyimide surface of an alignment film, the reactive monomer of liquid crystal contains a fluoro group (F—) and has a molecular formula, as follows:

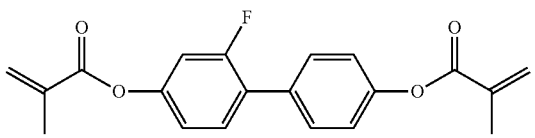
(III)

In the present invention, the liquid crystal composition is a liquid crystal composition of a one-drop filling (ODF) technology, and one of functions of the reactive monomer of liquid crystal is to help to control liquid crystal.

Figure 1A:
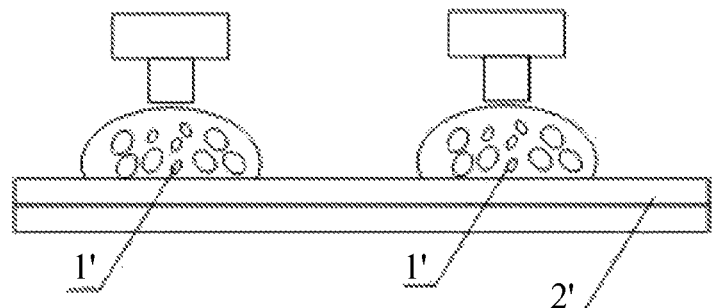
FIG. 1A is a schematic view of a traditional one-drop filling (ODF) technology dropping a liquid crystal composition onto an alignment film of a transparent substrate.
Figure 1B:
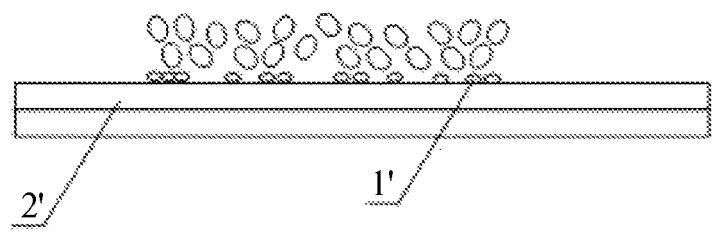
FIGS. 1B and 1C are schematic views of reactive monomers of liquid crystal in the liquid crystal composition deposited on a polyimide surface of the alignment film.
Figure 1C:
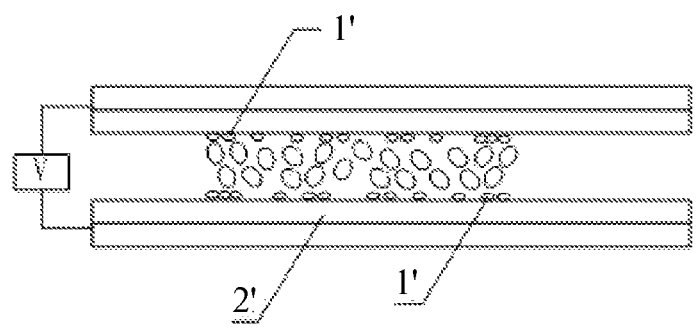
Figure 2A:
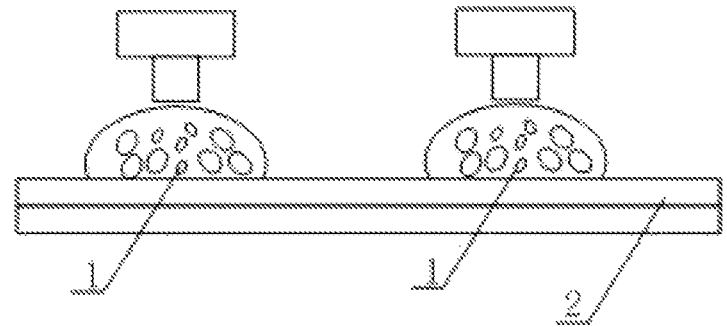
FIGS. 2A to 2C are schematic views of a one-drop filling (ODF) technology dropping a liquid crystal composition of the present invention onto an alignment film of a transparent substrate according to a preferred embodiment of the present invention.
Figure 2B:
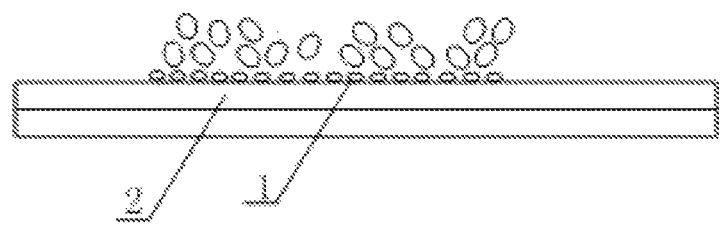
Figure 2C:
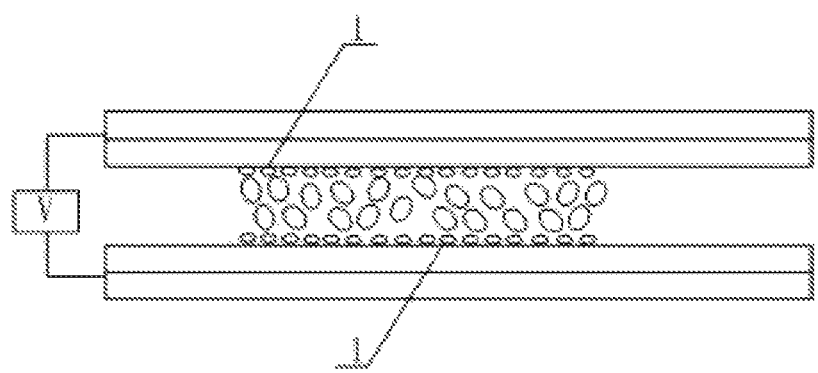

For more details, referring now to FIGS. 2A to 2C, schematic views of a one-drop filling (ODF) technology dropping a liquid crystal composition of the present invention onto an alignment film of a transparent substrate according to a preferred embodiment of the present invention are illustrated, wherein the ODF technology is used to add the liquid crystal composition containing a reactive monomer (RM) 1 of liquid crystal (i.e. smaller particles) into a space between two transparent substrates, and to apply voltage onto opposite transparent electrode layers of the two transparent substrates for polymerizing the reactive monomer of liquid crystal, wherein the reactive monomer 1 of liquid crystal is used to help to control a predetermined inclined angle of the liquid crystal composition.

Referring now to Tab. 2, observed results of the phenomenon of drop Mura defect for of the reactive monomer 1 of liquid crystal having the fluoro group (F—) of the present invention under conditions of various cell gaps of liquid crystal are shown in Tab. 2. Apparently, in comparison with Tab. 1 and Tab. 2, the reactive monomer of liquid crystal having the fluoro group (F—) of the present invention can overcome defects of the traditional reactive monomer of liquid crystal. When the cell gap of the liquid crystal is smaller than 3.8 μm, the reactive monomer of liquid crystal having the fluoro group (F—) of the present invention can improve the phenomenon of drop Mura defect.

TABLE 1

| Cell gap | reactive monomer | phenomenon of drop Mura defect |
|---|---|---|
| 3.8 μm | molecular formula (III) | Fewer |
| 3.5 μm | molecular formula (III) | Few |
| 3.3 μm | molecular formula (III) | Few |
| 3.0 μm | molecular formula (III) | Few |

For more details, in the present invention, hydrocarbon bonds of a side chain of polyimide (PI) surface of an alignment film has a fluorophobic effect, so that the fluoro group of the reactive monomer of liquid crystal can lower the interaction between the polyimide (PI) surface of the alignment film and the reactive monomer (RM) of liquid crystal to thus evenly deposit the liquid crystal composition containing the reactive monomers of liquid crystal onto the polyimide (PI) surface of the alignment film, so as to avoid from occurring the phenomenon of drop Mura defect occurred during implementing the ODF technology.

The present invention has been described with a preferred embodiment thereof and it is understood that many changes and modifications to the described embodiment can be carried out without departing from the scope and the spirit of the invention that is intended to be limited only by the appended claims.

The invention claimed is:

1. A liquid crystal panel, having a transparent substrate and an alignment film, characterized in that: a polyimide surface of the alignment film is dispersed with at least one type of reactive monomer of liquid crystal, the reactive monomer of liquid crystal causes the liquid crystal composition to be dispersed onto the polyimide surface of the alignment film, the reactive monomer of liquid crystal has a molecular formula, as follows:

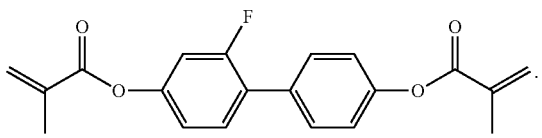 [SMILES: C=C(C)C(=O)Oc1ccc(-c2ccc(OC(=O)C(=C)C)cc2F)cc1]

2. The liquid crystal panel according to claim 1, characterized in that: the liquid crystal composition is a liquid crystal composition of a one-drop filling technology.

3. The liquid crystal panel according to claim 1, characterized in that: the transparent substrate is a glass substrate.

4. The liquid crystal panel according to claim 1, characterized in that: the transparent substrate is a flexible polymer substrate.

* * * * *